United States Patent [19]

Young

[11] 4,298,547

[45] Nov. 3, 1981

[54] PREPARATION OF IMPROVED ALKYLPHENYLSULFONATES

[75] Inventor: Lewis B. Young, Skillman, N.J.

[73] Assignee: Mobil Oil Corporation, New York, N.Y.

[21] Appl. No.: 176,367

[22] Filed: Aug. 8, 1980

Related U.S. Application Data

[62] Division of Ser. No. 61,222, Jul. 27, 1979, Pat. No. 4,234,751.

[51] Int. Cl.$^3$ .................................................. C07C 143/24
[52] U.S. Cl. ................................. 260/505 A; 585/323
[58] Field of Search ..................... 260/505 A; 585/323

[56] References Cited

U.S. PATENT DOCUMENTS 3,342,888  9/1967  DeWitt et al. ................. 260/505 A
3,352,933  11/1967  Sorgenti ........................ 260/505 A

*Primary Examiner*—Alan Siegel
*Attorney, Agent, or Firm*—C. A. Huggett; R. J. Cier; G. W. Allen

[57] ABSTRACT

An improved process for production of phenylalkylsulfonate compounds whereby the proportion of the 2-alkylphenylsulfonate isomer is reduced relative to the higher numbered isomers thereof (3-alkyl; 4-alkyl; etc.). After alkylation of aromatic compounds to produce a mixture of alkylbenzenes, the 2-alkylbenzene isomer is selectively cracked to lower boiling products, leaving the higher numbered isomers substantially unreacted. Subsequent sulfonation results in alkylphenylsulfonate derivatives having improved detergency properties.

8 Claims, No Drawings

PREPARATION OF IMPROVED ALKYLPHENYLSULFONATES

CROSS-REFERENCE TO RELATED APPLICATION

This is a Continuation-In-Part of U.S. Application Ser. No. 61,222, filed July 27, 1979, now U.S. Pat. No. 4,234,751, issued Nov. 18, 1980.

BACKGROUND OF THE INVENTION

1. Field of the Invention

The present invention relates to improved alkylphenylsulfonate detergent compounds. In particular, it is concerned with a method of producing alkylphenylsulfonates having reduced 2-alkylphenylsulfonate isomer content.

2. Description of the Prior Art

Linear alkylbenzene sulfonates containing alkyl side chains of approximately 8 to 16 carbon atoms in length are used as surface active agents in commercial detergent compositions. The scientific literature on the subject has indicated that the average location on the alkyl chain of the phenyl group can have significant and important effects on the detergency properties of the sulfonate. It has been found that by minimizing attachment of the aromatic ring to the alkyl chain at the #2 and #3 carboon atom positions and maximizing the content of isomers having a more centrally located phenyl group is of particular benefit with respect to important detergency considerations. For instance, it has been demonstrated in studies of various dodecylphenylsulfonate isomers and mixtures that one may achieve significant increases in solubility, wetting power and foaming power merely by shifting the average phenyl group location to more internal positions on the alkyl chain. [Tjepkena et al., 5th World Petroleum Congress, Sect. 4, No. 21 (1959).]

Alkylphenylsulfonates are commonly prepared from alkylbenzene compounds, the position of the phenyl group in the intermediate being fixed during the initial reaction of benzene with the linear olefin. The production of the alkylbenzene is conventionally carried out in the presence of a Friedel-Crafts catalyst (e.g. $AlCl_3$) to yield a mixture of all of the possible positional isomers. Attempts to reduce the external alkylbenzene isomer concentration (i.e. the 2-alkylbenzene), and thereby increase the relative concentration of the more desirable internal isomers (3-alkylbenzene; 4-alkylbenzene; etc.), have been reported, but only small reductions of the 2-alkylbenzene isomer content have been achieved.

SUMMARY OF THE INVENTION

The herein disclosed invention comprises a three-step process for preparation of linear alkylbenzene sulfonate compounds of reduced 2-alkylphenylsulfonate isomer content. The first (alkylation) and third (sulfonation) steps employ conventional technology for carrying out the respective reactions. The intermediate or second step capitalizes on the unique and selective cracking activity of a particular type of zeolite material to remove some or all of the 2-alkylbenzene isomer from the product of the alkylation step without significant loss of the more desirable internal isomers (i.e. 3-alkyl, 4-alkyl, etc.).

In the alkylation reaction, Step [1], an aromatic compound (e.g. benzene) and an alkylating agent (e.g. an olefin or alkylhalide) are brought into contact with an alkylation catalyst, under conditions of temperature and pressure conducive to promotion of the alkylation reaction, to produce alkylbenzene compounds. The reaction may be carried out in the presence of any known alkylation catalyst, many of which are conventionally classified as Lewis acids and Brönsted acids. When a known, conventional alkylation catalyst is utilized, the reactants are brought into contact therewith under conditions of temperature and pressure appropriate to that catalyst.

In a preferred embodiment the alkylation comprises a novel type of crystalline zeolite catalyst characterized by a silica to alumina mole ratio of at least about 12 and a constraint index, as hereinafter defined, within the approximate range of 1 to 12. In this embodiment it is contemplated that the alkylating reaction will most advantageously be carried out at temperatures within the approximate range of about 100° C. to 350° C. Particularly preferred zeolite alkylation catalysts are ZSM-5 and ZSM-12. Contemplated alkylating agents include structures having from about 6 to about 20 carbon atoms in the alkylating group and, preferably, will be linear. Olefins and alkylhalides are particularly preferred.

The second step of the process involves contacting the mixed alkylbenzene product of the alkylation reaction with a particular type of shape-selective crystalline zeolite material at temperature and pressure conditions conducive to the cracking reaction. Upon contact with the zeolite the 2-alkylbenzene compounds are selectively cracked to yield benzene, olefins, and lower molecular weight alkylbenzenes, while leaving the other positional isomers substantially unreacted. The novel class of zeolites useful herein can be characterized as having a silica to alumina mole ratio of at least about 12 and a constraint index, as hereinafter defined, of from 1 to 12. Selective cracking is effectively accomplished at temperatures of between about 150° C. and about 550° C. and at pressures of from about $10^4$ $N/m^2$ to about $10^6$ $N/m^2$ (0.1–10 atmospheres).

The final step comprises sulfonation of the product of Step [2] to convert the alkylbenzene compounds to their alkylphenylsulfonate derivatives. The reaction is well known and may be carried out by any conventional procedure, such as contacting the organic compound with sulfuric acid at temperatures of between about −7° C. and about +60° C.

The reaction products of the various steps may, if desired, be purified, concentrated, partially or wholly recycled, or solvents or contaminants removed therefrom before proceeding to the next succeeding step in the process, thereby maximizing the efficiency and/or yield of each of the respective steps.

DESCRIPTION OF SPECIFIC EMBODIMENTS

To facilitate the detailed explanation and understanding of the invention, the process will be broken down to its three component steps and each will be discussed separately. It must be realized, of course, that the process of the present invention comprises the sum total of its step and that the following separate discussions of the individual steps is merely for the sake of conveying a clear understanding of the entire process.

Step [1]-Alkylation of the Aromatic Compound:

The alkylation reaction is carried out by contacting the aromatic compound and the alkylating agent with an alkylation catalyst, which may comprise any of the conventional alkylation catalysts loosely classified as Lewis and Brönsted acids. The conventional alkylation catalysts utilized herein may comprise any conventional catalyst designed to promote the alkylation of aromatic compounds with, for instance, olefins. A partial listing of materials known to promote alkylation of aromatics, which is not intended to be comprehensive of all the catalytic materials utilizable herein, would include $AlCl_3$; $AlCl_3.HCl$; $AlCl_3.H_2O$; $AlBr_3$; $FeCl_3$; $SnCl_4$; $TiCl_4$; $ZrCl_4$; $BF_3$-$Et_2O$; $PF_5$; $H_2SO_4$; $CH_3SO_3H$; Amberlyst-15 (ion exchange resin); $P_2O_5$; $H_3PO_4$/kieselguhr; $SiO_2.Al_2O_3$; $BF_3.Al_2O_3$; $EtAlCl_2.H_2O$; and so forth. A more complete exposition of alkylation catalysts utilizable in the alkylation step of the hereindisclosed process, along with discussion of suitable reaction parameters for each, may be found in the treatise by G. A. Olah entitled *Friedel-Crafts and Related Reactions*, Vol. II (published by Interscience, 1963). Broadly speaking, such catalysts will promote the contemplated alkylation reaction at temperatures ranging from about minus 50° C. to about plus 200° C. and pressures from about $5 \times 10^4$ N/m² to about $10^6$ N/m² (0.5–10 atm.) and greater. Preferred reaction conditions include temperatures of between about 0° C. and about 150° C. and ambient pressure.

In a particularly preferred embodiment of Step [1], the alkylation catalyst utilized herein comprises a specific and novel type crystalline zeolite catalyst having unusual alkylation properties. Said zeolite catalyst is characterized by silica to alumina ratio of at least about 12 and a constant index, as hereinafter more fully defined, of from about 1 to about 12. Contemplated appropriate reaction conditions include a zeolite catalyst bed temperature of between approximately 100° C. and 400° C. and a pressure of from about $10^5$ N/m² to about $4 \times 10^6$ N/m², although temperatures of between about 200° C. and 350° C. and operating pressures between about $10^6$ and $3.5 \times 10^6$ N/m² are preferred. The reactants are most frequently passed across the catalyst, which comprises a bed of particulate material containing a crystalline zeolite catalyst as characterized above, as a continuous stream at a feed weight hourly space velocity (WHSV) of between about 1 hr$^{-1}$ and about 100 hr$^{-1}$. The latter WHSV is based upon the total weight of the catalyst compositions, i.e., the total weight of active catalyst and binder therefor. Contact between the reactants and the catalyst bed is preferably carried out at a WHSV of between about 5 hr$^{-1}$ and about 12 hr$^{-1}$.

Any or all of the component steps of the process of this invention may be carried out as a batch-type, semi-continuous or continuous operation utilizing a fixed, fluidized or moving bed catalyst system. The catalyst, after use in a moving bed reactor, may be conducted to a regeneration zone wherein coke is burned from the catalyst in an oxygen-containing atmosphere (air, for example) at elevated temperature, after which the regenerated catalyst is recycled to the conversion zone for further contact with the charge stock. In a fixed bed reactor, regeneration is carried out in a conventional manner where an inert gas containing a small amount of oxygen (e.g. 0.5–2%) is used to burn the coke in a controlled manner.

The process may be carried out in a system wherein the reactants are in either the liquid or the vapor state, and the mixture of alkylating agent and aromatic compounds may be substantially pure (ie., contain no substantial quantity of hydrocarbon material other than said mixture of said alkylating and aromatic materials) or may contain substantial amounts of other hydrocarbon material. The latter situation is such as, for instance, would exist when some or all of the feed stream for the instant process also comprises the effluent stream of an earlier upstream process, e.g., a process for the commercial manufacture of olefinic or aromatic compounds. Also, the feed stream for the process of this invention may contain other insert materials as diluents or solvents. Suitable diluents include, but are not limited to: hydrogen, carbon dioxide, methane, ethane, propane, cyclohexane, etc.

The preferred alkylating agents for utilization in the process of this invention comprise olefins and alkylhalide compounds having from about 6 to about 20 carbon atoms in a linear chain. However, any hydrocarbon compound having an available alkyl group of approximately 6 to 20 carbon atoms, or capable of generating a reactive alkyl group, may be employed.

Step [2]-Selective Cracking:

Mild Friedel-Crafts alkylation of benzene with linear olefins produces a mixture of linear alkylbenzenes. For example, any of the linear dodecenes will produce substantially the same mixture of the five possible positional isomers of dodecylbenzene (2-dodecyl; 3-dodecyl; 4-dodecyl; 5-dodecyl; 6-dodecyl):

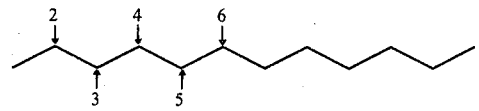

Similarly, reaction of benzene with octene is known to give a mixture of all three possible internal linear octylbenzenes:

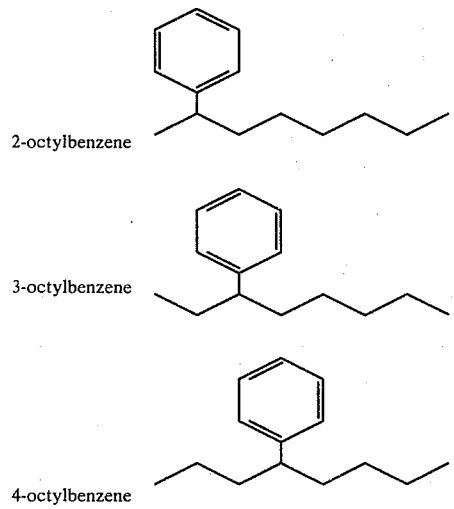

When mixtures of these linear octylbenzenes, dodecylbenzenes or other similarly linear alkylbenzenes are passed over the preferred crystalline zeolite catalysts defined below, highly selective cracking of the 2-isomer takes place, leaving the more internal isomers substantially unreacted and in excess of equilibrium.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs to the useful zeolites described herein, that is to say those zeolites having no measurable amount of aluminum (silica to alumina mole ratio of infinity) but which otherwise embody the characteristics disclosed.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re 29,948. The entire descriptions contained within those patents, particularly the X-ray diffraction pattern of therein disclosed JSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN:(0–1.5)$M_{2/n}$O:(0–2)$Al_2O_3$:(100)$SiO_2$ wherein:
M is at least one cation having a valence n; and
RN is a $C_1$–$C_{20}$ organic compound having at least one amine functional group of $pK_a \geq 7$.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN+H_2O$.

The characteristic X-ray diffraction pattern of the synthetic zeolite ZSM-48 has the following significant lines:

| Characteristic Lines of ZSM-48 | |
| --- | --- |
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | BROAD | PREFERRED |
| --- | --- | --- |
| $Al_2O_3/SiO_2$ | = 0 to 0.02 | 0 to 0.01 |
| $Na/SiO_2$ | = 0 to 2 | 0.1 to 1.0 |
| $RN/SiO_2$ | = 0.01 to 2.0 | 0.05 to 1.0 |
| $OH^-/SiO_2$ | = 0 to 0.25 | 0 to 0.1 |
| $H_2O/SiO_2$ | = 10 to 100 | 20 to 70 |
| $H^+$(added)/$SiO_2$ | = 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pK_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, ZSM-48, offretite, and isotypes thereof, with ZSM-5 being particularly preferred.

In a preferred aspect of this invention, the zeolites hereof are selected as those providing among other things a crystal framework density, in the dry hydrogen form, of not less than about 1.5 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.5 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in *PROCEEDINGS OF THE CONFERENCE ON MOLECULAR SIEVES*, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.5 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0 > 28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |

| | Void Volume | Framework Density |
|---|---|---|
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The preferred crystalline zeolite catalysts useful herein may desirably be modified by treatment which entails steaming of the zeolite by contact with an atmosphere containing from about 5% to about 100% steam at a temperature of about 250° C. to about 1000° C. for a period of between about 0.25 to about 100 hours and under pressures ranging from subatmospheric to several hundred atmospheres.

Another modifying treatment involves precoking of the catalyst to deposit a coating of between about 2 and about 75 wt. %, and preferably between about 15 and 75 wt.% of coke thereon. Precoking can be accomplished by contacting the catalyst with a hydrocarbon charge, e.g. toluene, under high severity conditions or, alternatively, at a reduced hydrogen to hydrocarbon concentration (i.e. 0 to 1 mole ratio of hydrogen to hydrocarbon) for a sufficient time to deposit the desired amount of coke thereon.

The process of Step [2] is carried out by bringing the mixture of alkylbenzenes into contact with the crystalline zeolite catalyst at conditions of temperature and pressure conducive to bringing about the cracking reaction. Temperatures of about 150° C. to 550° C. are suitable, but it is preferable that the process be carried out at between about 200° C. The pressure may be from about $10^4$ N/m$^2$ to about $10^6$ N/m$^2$ (0.1–10 atmospheres) and preferably between about $5 \times 10^4$ N/m$^2$ and about $5 \times 10^5$ N/m$^2$ (0.5–5 atmospheres). The alkylbenzene mixture may be neat, i.e. devoid of diluents, when brought into contact with the catalyst or it may be diluted with other, preferably hydrocarbon, material which acts as a diluent and carrier.

Subsequent to the selective reaction of the 2-alkylbenzene constituent of the alkylbenzene mixture, the unreacted higher alkylbenzenes (i.e., the 3-alkylbenzenes, 4-alkylbenzenes, may be recovered by conventional methods, such as distillation.

Step [3] —sulfonation:

Alkylbenzenes may be converted to alkylphenylsulfonates by sulfonation of the aromatic ring with sulfuric acid. The reaction is well known in the art and is commonly carried out by contacting the organic compound with sulfuric acid at temperatures of from about −70° C. to about +60° C. Detailed descriptions of specific commercial processes abound in the literature—see, for instance, pages 60–62 of *INDUSTRIAL CHEMICALS*, Third Edition, by W. L. Faith et al, published by John Wiley & Sons, Inc., 1966—and those skilled in the field need only refer to the conventional literature for instruction on how to carry out such reactions.

As discussed above, Steps [1] and [3] of the hereindisclosed process employ well-known, conventional technology. It is expected that those of normal skill in the chemical arts will need no further instruction with regard to techniques for carrying out these individual steps since the chemical literature and text books abound with suitable teachings. The following examples are presented for the purposes of illustrating the crucial second step (selective cracking) of the process, so that those skilled in the art may better understand this process. The examples should not, however, be interpreted as placing undue limitations on the process.

EXAMPLE 1

A mixture of octylbenzenes was prepared by alkylation of benzene with a 1-octene/trans-4-octene mixture in the presence of AlCl$_3$ catalyst at a temperature and pressure of 50° C. and one atmosphere (absolute), respectively. The reaction product, comprising 11.7% 2-octylbenzene, 6.2% 3-octylbenzene, 5.0% 4-octylbenzene and 77.0% benzene, was recovered and utilized as the feed in the following selective cracking reactions.

EXAMPLE 2

The octylbenzene in benzene mixture from Example 1 was passed over 1.0 gram of HZSM-5 zeolite catalyst at 350° C. and atmospheric pressure and at a feed weight hourly space velocity (WHSV) of 7. The product analysis is given in Table I below.

TABLE I

| | Feed | Product | $\phi$-C$_8$ Isomer Loss |
|---|---|---|---|
| 2-Octylbenzene | 11.7% | 0.06% | 99.5% |
| 3-Octylbenzene | 6.2% | 6.2% | 1% |
| 4-Octylbenzene | 5.0% | 5.0% | |
| Benzene | 77.0% | 72.6% | |
| | — | 13.3% | |
| 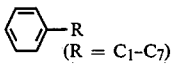 (R = C$_1$-C$_7$) | | | |
| Olefins | — | 2.7% | |

The 2-octylbenzene component of the feed stream has been selectively cracked to the extent of 99.5% of that present in the feed stream. However, it will be noted that only 1% of the total of the 3-octyl plus the 4-octyl isomers has been cracked.

EXAMPLE 3

This was a repeat of Example 2, except the HZSM-5 catalyst was steamed for 2 hours at 600° C. and 1 atmosphere pressure prior to use. The results are given in Table II.

TABLE II

| | Feed | Product | $\phi$-C$_8$ Isomer Loss |
|---|---|---|---|
| 2-Octylbenzene | 11.7% | 0.06% | 99.5% |
| 3-Octylbenzene | 6.2% | 6.2% | <1% |
| 4-Octylbenzene | 5.0% | 5.0% | |
| Benzene | 77.0% | | |
| | — | | |
| 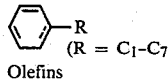 (R = C$_1$-C$_7$) | | | |
| Olefins | — | | |

EXAMPLE 4

The octylbenzene in benzene mixture of Example 1 was passed across 1.0 grams HZSM-12 zeolite catalyst at 275° C., 1 atmosphere of pressure and a WHSV of 44. The product analysis is given below.

TABLE III

| | Feed | Product | $\phi$-C$_8$ Isomer Loss |
|---|---|---|---|
| 2-Octylbenzene | 11.7% | 0.85% | 93% |
| 3-Octylbenzene | 6.2% | 4.9% | |
| 4-Octylbenzene | 5.0% | 5.1% | |
| Benzene | 77.0% | 80.2% | |
| | — | 4.65% | |
| 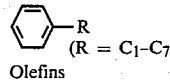 (R = C$_1$-C$_7$) | | | |
| Olefins | — | 4.2% | |

EXAMPLES 5-8

Samples of Offretite, Mordenite (de-aluminized), and Beta zeolites, as well as a conventional SiO$_2$.Al$_2$O$_3$ cracking catalyst, were tested in the same manner as the foregoing examples. The results are given in Tables IV–VII.

TABLE IV

Example 5
Catalyst: Offretite
Temp.: 275° C.
Press.: Atm.
WHSV: 5

| | Feed | Product | $\phi$—C$_8$ Isomer Loss |
|---|---|---|---|
| 2-Octylbenzene | 12.5% | 1.3% | 89.6% |
| 3-Octylbenzene | 6.8% | 5.6% | 17.7% |
| 4-Octylbenzene | 5.5% | 5.5% | 0% |
| Benzene | 74.9% | | |
| 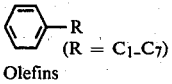 (R = C$_1$-C$_7$) | | | |
| Olefins | — | | |

Offretite, much like the ZSM-5 and ZSM-12 zeolites of the previous examples, is shown to have desirable selectivity to reaction of the 2-octyl isomer with only slight reaction of the 3-octylbenzene. Virtually none of the 4-octylbenzene has been reacted.

TABLE V

Example 6
Catalyst: Mordenite (-Al)
Temp.: 250° C.
Press.: Atm.
WHSV: 5

| | Feed | Product | $\phi$—C$_8$ Isomer Loss |
|---|---|---|---|
| 2-Octylbenzene | 11.7% | 1.75 | 85.5% |
| 3-Octylbenzene | 6.3% | 4.0% | 36.5% |
| 4-Octylbenzene | 5.1% | 4.6% | 9.8% |
| Benzene | 76.1% | 79.7% | |
| | — | 5.0% | |
| 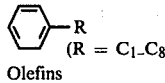 (R = C$_1$-C$_8$) | | | |
| Olefins | — | 2.7% | |

TABLE VI

Example 7
Catalyst: Beta Zeolite
Temp.: 300° C.
Press.: Atm.
WHSV: 5

| | Feed | Product | $\phi$-C$_8$ Isomer Loss |
|---|---|---|---|
| 2-Octylbenzene | 10.8% | 3.3% | 69.4% |
| 3-Octylbenzene | 5.85% | 4.3% | 26.5% |
| 4-Octylbenzene | 4.8% | 4.2% | 12.5% |
| Benzene | 77.85% | 85.2% | |
| | — | 1% | |
| 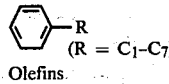 (R = C$_1$-C$_7$) | | | |
| Olefins | — | 1.3% | |

TABLE VII

Example 8
Catalyst: SiO$_2$ . Al$_2$O$_3$
Temp.: 350° C.
Press.: Atm.
WHSV: 6

| | Feed | Product | $\phi$-C$_8$ Isomer Loss |
|---|---|---|---|
| 2-Octylbenzene | 11.4% | 2.6% | 77.2% |
| 3-Octylbenzene | 6.1% | 2.1% | 65.6% |
| 4-Octylbenzene | 5.0% | 2.0% | 60.0% |
| Benzene | 77.0% | 83.1% | |
| | — | 2.5% | |
| 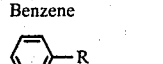 (R = C$_1$-C$_7$) | | | |

TABLE VII-continued

Example 8
Catalyst: SiO$_2$ . Al$_2$O$_3$
Temp.: 350° C.
Press.: Atm.
WHSV: 6

|         | Feed | Product | φ-C$_8$ Isomer Loss |
|---------|------|---------|---------------------|
| Olefins | —    | 7.7%    |                     |

As will be seen, the catalysts of Examples 6–8 were not appreciably selective toward the 2-octylbenzene. Table VIII below summarizes the selectivity of the tested catalysts using the ratio of the cracking rate constants k as an indicium of selectivity toward the 2-octylbenzene relative to the 3-and 4-octylbenzene.

TABLE VIII

| Example | Catalyst         | φ—C$_8$ Cracking Selectivity k$_{(2)}$/k$_{(3+4)}$ |
|---------|------------------|----------------------------------------------------|
| 2       | HZSM-5           | >350                                               |
| 3       | HZSM-5 (steamed) | >500                                               |
| 4       | HZSM-12          | 21                                                 |
| 5       | Offretite        | 22                                                 |
| 6       | Mordenite (-Al)  | 7                                                  |
| 7       | Beta             | 5                                                  |
| 8       | SiO$_2$ . AlO$_3$ | 1.5                                               |

EXAMPLES 9–13

In the same manner as the foregoing examples, a sample of mixed dodecylbenzenes in benzene was passed over various cracking catalysts at temperatures ranging between 200° C. and 300° C. The feed composition comprised:

| 2-Dodecylbenzene | 9.74% |
|------------------|-------|
| 3-Dodecylbenzene | 5.32% |
| 4-Dodecylbenzene | 4.09% |
| 5-Dodecylbenzene | 4.16% |
| 6-Dodecylbenzene | 3.95% |

Table IX below is a summary of the cracking activity of the catalysts, using the pseudo first order rates of cracking of the 2-isomer relative to the 3-isomer as a measure of the catalyst shape selectivity.

TABLE IX

| Example | Catalyst         | Dodecylbenzene Reacted | k$_{(2)}$/k$_{(3)}$ |
|---------|------------------|------------------------|---------------------|
| 9       | HZSM-5           | 99.0%                  | 400                 |
| 10      | HZSM-5 (steamed) | 99.1%                  | 400                 |
| 11      | HZSM-12          | 94.5%                  | 8                   |
| 12      | Offretite        | 89%                    | 7                   |
| 13      | Mordenite (-Al)  | 94%                    | 4                   |

The examples demonstrate the very high degree of shape selectivity of the most preferred catalyst (HZSM-5) as compared to a non-shape-selective catalyst (SiO$_2$.Al$_2$O$_3$) and various partially shape-selective catalysts, including dealuminized mordenite which is outside the scope of this invention.

Although the foregoing examples will illustrate some preferred embodiments of the disclosed process, it is of course to be understood that numerous variations can be resorted to without departing from the spirit and scope of this invention, as those having normal skill in the art will readily appreciate.

I claim:

1. In the process for making alkylbenzene sulfonate compounds comprising:
   (A) alkylation of aromatic compounds to produce alkylbenzene compounds wherein the alkyl group has between about 6 and about 20 carbon atoms therein, followed by
   (B) sulfonation of the alkylbenzene compounds to produce the alkylphenylsulfonate derivative thereof;
   the improvement comprising selective production of alkylphenylsulfonates having reduced proportion of the 2-alkylphenylsulfonate isomer thereof; said improvement resulting from contact of the isomeric mixture of alkylbenzene compounds produced in Step (A) above, prior to carrying out Step (B) above, with a crystalline zeolite catalyst having a constraint index of about 1 to 12 and a silica to alumina mole ratio of at least 12, at a temperature of between about 150° C. and 550° C. and a pressure of between about 10$^4$N/m$^2$ and 10$^6$N/m$^2$.

2. The process of claim 1 wherein said crystalline zeolite catalyst is chosen from the group consisting of ZSM-5, ZSM-11, ZSM-12, ZSM-23, ZSM-35, ZSM-38, ZSM-48 and offretite.

3. The process of claim 1 wherein said alkylphenylsulfonate comprises dodecylbenzenesulfonate.

4. The process of claim 1 wherein said temperature is between 200° C. and 400° C. and said pressure is between 5×10$^4$N/m$^2$ and 5×10$^5$N/m$^2$.

5. The process of claim 1 wherein said zeolite is ZSM-5.

6. The process of claim 1 wherein said zeolite is ZSM-23.

7. The process of claim 1 wherein said zeolite is offretite.

8. The process of claim 1, 2, 3, 4, 5, 6 or 7 wherein said zeolite catalyst additionally comprises a binder therefor.

* * * * *

UNITED STATES PATENT AND TRADEMARK OFFICE
CERTIFICATE OF CORRECTION

PATENT NO. : 4,298,547
DATED : November 3, 1981
INVENTOR(S) : Lewis B. Young

It is certified that error appears in the above—identified patent and that said Letters Patent is hereby corrected as shown below:

Abstract, line 1, "phenylalkylsulfonate" should be --alkylphenylsulfonate--

Column 1, line 28, "carboon" should be --carbon--

Column 7, line 44, "JSM-5" should be --ZSM-5--

Signed and Sealed this

Twenty-second Day of June 1982

[SEAL]

Attest:

GERALD J. MOSSINGHOFF

Attesting Officer     Commissioner of Patents and Trademarks